(12) United States Patent
Wassmann-Wilken et al.

(10) Patent No.: US 7,101,997 B2
(45) Date of Patent: Sep. 5, 2006

(54) METHOD FOR PRODUCING PHENOTHIAZINIUM COMPOUNDS

(75) Inventors: Suzanne Wassmann-Wilken, Hannover (DE); Reinhard Knieps, Hannover (DE); Thomas Potrawa, Seelze (DE); Andreas Kanschik-Conradsen, Garbsen (DE); Joachim Schulz, Pohle (DE); Christian Werner, Hannover (DE)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/960,811

(22) Filed: Oct. 7, 2004

(65) Prior Publication Data

US 2006/0079682 A1    Apr. 13, 2006

(51) Int. Cl.
*C07D 279/18*    (2006.01)
(52) U.S. Cl. .............................. 544/37; 544/35; 544/36
(58) Field of Classification Search ................... 544/37
See application file for complete search history.

(56) References Cited

U.S. PATENT DOCUMENTS

| 3,641,016 A | 2/1972 | Korosi et al. |
| 2003/0180224 A1 | 9/2003 | Brown et al. |

FOREIGN PATENT DOCUMENTS

WO    WO 02/096896    12/2002

OTHER PUBLICATIONS

Photochemistry and Photobiology, *In Vitro Photodynamic Activity of a Series of Methylene Blue Analogues*, Mellish et al., 392-397 (2002).
The Royal Society of Chemistry and Owner Societies, *A Comparative Analysis of Phenothizinium Salts for the Photosensitisation of Murine Fibrosarcoma (RIF-1) Cells in Vitro*, Walker et al., 653-569 (2004).
Department of Chemistry, Georgia State University, *A Synthetic Route to 3(Dialkylamino)phenothizin-5-ium Salts and 3,7-Disubstituted Derivatives Containing Two Different Amino Groups*, Strekowski et al., 1693-1695, (1993).
Journal of Colloid and Interface Science, *Monolayer Films of Surfactant Derivatives of Methylene Blue*, General Electric Company, Corporate Research and Development, 486-490 (1999).
Journal of Chromatography, *Thin-Layer Chromatographic Separation of Methylene Blue and Related Thiazine Dyes*, K.W. Loach, 119-126 (1971).
Chemical Laboratory of Iowa State University, *The Addition of Deuterium Bromide to 1,3-Cyclohexadiene*, Hammond et al. 2554-2559 (1960).
American Chemical Society, *Synthesis and AntiTumor Activity of Wuaternary Ellipticine Glycosides, a Series of Novel and Highly Active AntiTumor Agents*, Honda et al., 1295-1305 (1988).
The Journal of Histochemistry and Cytochemistry, *Chromatographic Separation and Isolation of Metachromatic Thiazine Dyes*, K.D. Taylor, 248-257 (1960).
Pathology Research Laboratory, University of Bristol, "*Chromatographic Separation and Isolation of Metachromatic Thizine Dyes*", 248-257.
Tetrahedron, vol. 53. No. 29, *Synthesis of Substituted Phenothizines Analogous to Methylene Blue by Electrophilic and Nucleophilic Aromatic Substitutions in Tandem. A Mechanistic Perspective.*, Leventis et al., 10083-10092 (1997).

Primary Examiner—Kahsay Habte
(74) Attorney, Agent, or Firm—Deborah M. Chess

(57) ABSTRACT

A process for producing a phenothiazinium compound comprising the step of: reacting phenothiazine, in the presence of a halogen, with at least one amine selected from the group consisting of:

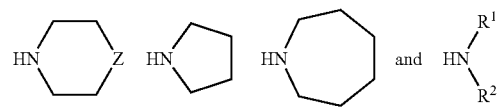

wherein Z is $CH_2$, O, S, $SO_2$, NH, $NCH_3$, $NC_2H_5$, $NCH_2CH_2OH$ or $NCOCH_3$, and $R^1$ and $R^2$ are each independently linear or branched $C_nH_{2n}Y$.

18 Claims, No Drawings

METHOD FOR PRODUCING PHENOTHIAZINIUM COMPOUNDS

BACKGROUND OF THE INVENTION

1. Field of the Invention

The present invention generally relates to a novel one step halogenation/amination synthesis for producing phenothiazinium compounds from phenothiazine.

2. Discussion of the Background Art

There has been recent advances in the use of compounds having a photosensitizing chromophoric system, a sulphonamido functionality and a carboxy functionality as a photosensitizer in photodynamic therapy (PDT), in photochemical internalization in the production of a cancer vaccine or in the diagnosis or detection of medical conditions.

These photosensitizing chromophoric systems are preferably residue of a metal-free phthalocyanine, a methyl phthalocyanine, a benzoporphyrin, a purpurin, a chlorin, a bacteriochlorin, a tetraarylporphyrin, a porphycene or a texaphyrin, more preferably a residue of a metal phthalocyanine, a chlorin or a bacteriochlorin, especially a residue of a metal phthalocyanine, as set forth in US-2003/0180224, which is incorporated herein in its entirety.

Such phenothiazinium compounds are disclosed in WO-02/096896 as comprising the following formula (I):

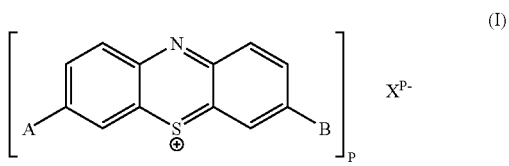

wherein A and B are each independently selected from the group consisting of:

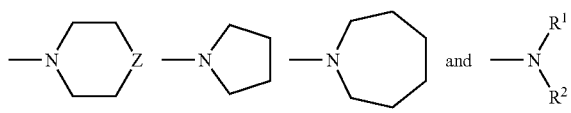

wherein Z is $CH_2$, O, S, $SO_2$, NH, $NCH_3$, $HC_2H_5$, $NCH_2CH_2OH$ or $HCOCH_3$ and $R^1$ and $R^2$ are each independently linear or branched $C_nH_{2n}Y$, where n is 1–6, Y is H, F, Cl, Br, I, OH, $OCH_3$, $OC_2H_5$, $OC_3H_7$, CN or $OCOCH_3$, and where $X^{p-}$ is a counteranion and P is 1, 2 or 3.

Unfortunately, WO-02/096896 does not teach a commercially acceptable synthesis route for the manufacture of such phenothiazinium compounds, or any synthesis route for that matter.

K. J. Mellish et al. (Photochem. Photobiol., 2002, 75/4, 392–397) describes the synthesis of a series of tetraalkyl-iodide-derivatives of phenothiazine by an elaborate procedure. The phenothiazine is halogenated first and isolated, and then reacted at room temperature with the appropriate N,N-dialkylamine. The compounds are isolated by an elaborated work-up procedure using, e.g., halogenated solvents and only characterized by mass spectrometry. The purity cannot be derived from the data given.

N. Leventis et al. (Tetrahedron, 1997, 53/29, 10083–10092) describes the synthesis of a series of thiazine dyes. The synthesis is performed in two steps by halogenating phenothiazine in glacial acetic acid and then reaction with the corresponding amine in ethanol. The last step requires workup with chloroform and then isolation by column chromatography using chloroform/MeOH. The evaporation of the organic fractions is followed by recrystallization. This extensive procedure is not practicable for a large-scale synthesis.

L. Strekowski et al. (J. Heterocycl. Chem. 1993, 30/4, 1693–1695) describes the synthesis of dialkylamino-phenothiazin-derivatives with two different amino groups and $I_3^-$ as the counterion. The compounds are synthesized in a two-step synthesis.

K. W. Loach (J. Chrom., 1971, 60, 119–129) describes the purification and analysis of a series of thiazine dyes. It concedes that in former literature "published procedures appear to give incomplete resolution of complex mixtures or separate them very slowly." The paper describes only analytical separations, using mixtures of alcohol/chloroform/acetic acid which are disadvantageous because of the use of halogenated solvents and the mixture not being stable over more than 24 hours. Also, the separations had to be performed in the dark as the compounds showed significant photodecomposition. Also see U.S. Pat. No. 3,641,016 (Korosi et al.).

It would be desirable to develop a simple commercial synthesis for phenothiazinium compounds from phenothiazine.

The present invention preferably provides the following: an easy one-pot/one-step synthesis with crystallization right from the reaction mixture; eliminates the use of halogenated solvents and methanol during the reaction which also adds to process safety, as methanol/bromine mixtures are hazardous; eliminates the use of halogenated solvents and methanol in the workup; completely eliminates the need to use chromatography which is expensive, causes photodecomposition of material, requires the use of halogenated solvents and silica and causes inconsistent purity results; improves the yield using higher reaction temperature; and results in consistent, high purity yields which are reproducible.

SUMMARY OF THE INVENTION

The present invention is directed to a one step halogenation/amination procedure (e.g., bromination/amination) for producing phenothiazinium compounds from phenothiazine. This unique process eliminates the use of undesirable halogenated solvents throughout the synthesis process, since such a process typically requires the use of methanol in the halogenation step of phenothiazine which reacts violently with bromine.

A process for producing a phenothiazinium compound comprising the step of: reacting phenothiazine, in the presence of a halogen, with at least one amine selected from the group consisting of:

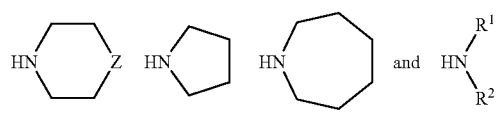

wherein Z is $CH_2$, O, S, $SO_2$, NH, $NCH_3$, $NC_2H_5$, $NCH_2CH_2OH$ or $NCOCH_3$, and $R^1$ and $R^2$ are each independently linear or branched $C_nH_{2n}Y$; provided that each amine is the same or different as the other amine.

The phenothiazinium compound preferably has the general formula:

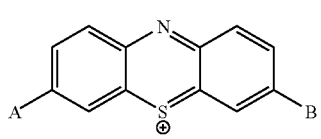
(I)

wherein A and B are each selected from the group consisting of:

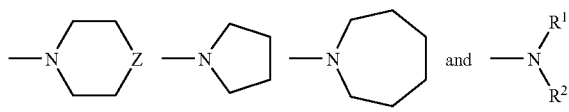
and wherein Z is $CH_2$, O, S, $SO_2$, NH, $NCH_3$, $NC_2H_5$, $NCH_2CH_2OH$ or $NCOCH_3$ and $R^1$ and $R^2$ are each independently linear or branched $C_nH_{2n}Y$, where n is 1–6, Y is H, F, Br, I, OH, $OCH_3$, $OC_2H_5$, $OC_3H_7$, CN or $OCOCH_3$, and where $X^-$ is a halide counteranion.

The halogen is selected from the group consisting of: bromine, iodine, chlorine and mixtures thereof. The amine is diiso- or di-n-alkylamine, e.g., diisopropylamine, diisobutylamine, diisopentylamine, di-n-propylamine, di-n-butylamine, di-n-pentylamine, or n-alkyl-iso-alkyl-amine, e.g., ethyl-isopropylamine.

It is preferable that the reaction occur at a temperature in the range between about −5° C. to +55° C., more preferably between about −5° C. to +20° C., and most preferably between about 50° C. to 55° C.

The starting material phenothiazine preferably has the formula:

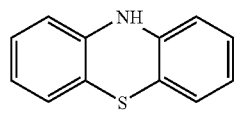

The process according to the present invention may further comprise the step of filtering the phenothiazinium compound.

It is preferable that the reaction is carried out in a single reactor, wherein the phenothiazine and amine are mixed together, followed by addition of the halogen.

Preferably, the present invention involves a process for producing a phenothiazinium compound comprising the step of: reacting phenothiazine, in the presence of a bromine, with at least one dialkylamine. According to this embodiment, the phenothiazinium compound has the general formula:

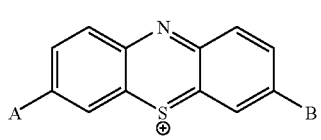
(I)

wherein A and B are each selected from the group consisting of:

wherein $R^1$ and $R^2$ are each independently linear or branched $C_nH_{2n}Y$, n is 1 to 6, and where $X^-$ is a bromide counteranion. Preferably, the dialkylamine is selected from the group consisting of: diisopropylamine, diisobutylamine, diisopentylamine, di-n-propylamine, di-n-butylamine, di-n-pentylamine, ethyl-isopropylamine and mixtures thereof.

DETAILED DESCRIPTION OF THE PREFERRED EMBODIMENT

The novel synthesis process according to the present invention is performed in a mixture of 1-propanol/THF and the bromination is performed in the presence of di-n-propylamine so that the amination takes place immediately after bromination in a simple one-pot/one-step synthesis process. The present invention also eliminates the need for isolation by extraction and/or chromatography, especially the elimination of chromatography due to the fact that it disadvantageously uses vast amounts of halogenated solvents and silica. The phenothiazinium compound synthesized according to the present invention crystallizes out of the reaction mixture and is harvested by simple filtration. The novel process according to the present invention results in a very high quality crystallized phenothiazinium compound (i.e., greater than 96% after crystallization determined by high performance liquid chromatography (HPLC)) versus 30–60% HPLC purity after conventional column chromatography). Another remarkable improvement uncovered by use of the unique synthesis process according to the present invention was the discovery that the yield may double when the reaction is performed at 50° C.; whereas the prior art processes are all performed at temperatures in the range of −5 to 20° C.

EXAMPLE 1

A 1 liter 3-necked flask was fit with a stirrer, thermometer, reflux condenser, 2-necked attachment and dropping funnel. The flask was charged at room temperature with 60 mL of THF, 60 mL of 1-propanol and 40.5 grams of di-n-propylamine (0.4 mol, 20 eq.). At room temperature, 10 grams of phenothiazine (0.05 mol, 1 eq.) were dissolved with stirring in the reaction mixture, resulting in a clear, almost colorless solution. The mixture was heated to 50° C. pot temperature with the aid of a water bath. 24 grams of bromine (0.15 mol, 3 eq.) were added over 30–40 minutes at 50–55° C. pot temperature via addition funnel. The mixture turned blue immediately. A precipitate was formed during the addition, and beige fumes evolved which did not migrate out of the flask. After the bromine-addition was completed, the mixture was stirred another 30 minutes at 50–55° C. and then cooled to 20–25° C. Under stirring, 100 mL toluene, 100 mL $H_2O$ and then 100 mL 1M aq. HBr were added. The mixture was slowly stirred at room temperature overnight and then filtered. The crystals were washed in portions with 100 mL $H_2O$ and then 50 mL toluene and dried at 50° C. on the rotavap (40 mbar) for about 2–3 hours. The yield was 5.2 grams (22%) of reddish, shimmering crystals 3,7-bis[di(n-propyl)amino]phenothiazin-5-ium bromide. HPLC-purity is greater than 96%.

EXAMPLE 2

The above-mentioned experimental procedure was also successfully applied to di-n-butylamine instead of di-n-propylamine, yielding 3,7-bis[di(n-butyl)amino]phenothiazin-5-ium bromide in 8% yield:

A 1 liter 3-necked flask was fit with a stirrer, thermometer, reflux condenser, 2-necked attachment and dropping funnel. The flask was charged at room temperature with 60 mL of THF, 60 mL of 1-propanol and 51.7 grams of di-n-butylamine (0.4 mol, 20 eq.). At room temperature, 10 grams of phenothiazine (0.05 mol, 1 eq.) were dissolved with stirring in the reaction mixture, resulting in a clear, almost colorless solution. The mixture was then heated to 50° C. pot temperature with the aid of a water bath. 24 grams of bromine (0.15 mol, 3 eq.) were then added over 30–40 minutes at 50–55° C. pot temperature via addition funnel. The mixture turned blue immediately. A precipitate was formed during the addition, and beige fumes evolved which did not migrate out of the flask. After the bromine-addition was completed, the mixture was stirred another 30 minutes at 50–55° C. and then cooled to 20–25° C. Under stirring, 100 mL toluene, 100 mL H$_2$O and then 100 mL 1M aq. HBr were added. The mixture was slowly stirred at room temperature, then the flask remained open under the fume hood at room temperature for 5 days. The mixture was filtered, the crystals were washed in portions with 100 mL H$_2$O and then 50 mL toluene and dried at 50° C. on the rotavap (40 mbar) for about 2–3 hours. The yield was 1.9 grams (8%) of reddish, shimmering crystals. HPLC-purity was greater than 96%.

What is claimed is:

1. A process for producing a phenothiazinium compound represented by the formula:

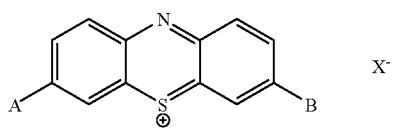

wherein A and B are each independently represented by the formula:

said process comprising the step of:
reacting phenothiazine, in the presence of a halogen, with an amine represented by the formula:

wherein R$^1$ and R$^2$ are each independently linear or branched C$_n$H$_{2n}$Y;

where n is 1–6, Y is H, F, Br, I, OH, OCH$_3$, OC$_2$H$_5$, OC$_3$H$_7$, CN or OCOCH$_3$; and
wherein X$^-$ is a halide counteranion.

2. The process according to claim 1, wherein said halogen is selected from the group consisting of: bromine, iodine, chlorine and mixtures thereof.

3. The process according to claim 1, wherein said amine is a dialkylamine selected from the group consisting of: diisoalkylamine, di-n-alkylamine and n-alkyl-iso-alkyl-amine.

4. The process according to claim 3, wherein said dialkylamine is selected from the group consisting of: diisopropylamine, diisobutylamine, diisopentylamine, di-n-propylamine, di-n-butylamine, di-n-pentylamine, ethyl-isopropylamine and mixtures thereof.

5. The process according to claim 1, wherein said reaction occurs at a temperature in the range between about −5° C. to 55° C.

6. The process according to claim 1, further comprising: filtering said phenothiazinium compound.

7. The process according to claim 1, wherein said reaction is carried out in a single reactor.

8. The process according to claim 7, wherein said phenothiazine and said amine are mixed together, followed by addition of said halogen.

9. The process according to claim 5, wherein said reaction occurs at a temperature in the range between about −5° C. to 20° C.

10. The process according to claim 5, wherein said reaction occurs at a temperature in the range between about 50° C. to 55° C.

11. A process for producing a phenothiazinium compound represented by the formula:

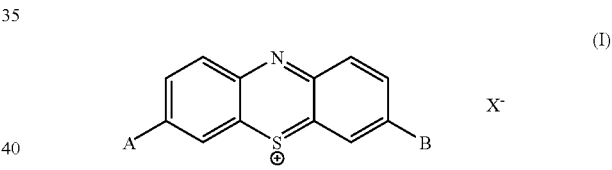

wherein A and B are each selected from the group consisting of:

wherein R$^1$ and R$^2$ are each independently linear or branched C$_n$H$_{2n}$Y, n is 1 to 6, and
where X$^-$ is a bromide counteranion;
said process comprising the step of:
reacting phenothiazine, in the presence of a bromine, with a dialkylamine represented by the formula:

wherein R$^1$ and R$^2$ are each independently linear or branched C$_n$H$_{2n}$Y; and
where n is 1–6, Y is H, F, Br, I, OH, OCH$_3$, OC$_2$H$_5$, OC$_3$H$_7$, CN or OCOCH$_3$.

12. The process according to claim 11, wherein said dialkylamine is selected from the group consisting of: diisopropylamine, diisobutylamine, diisopentylamine, di-n-propylamine, di-n-butylamine, di-n-pentylamine, ethyl-isopropylamine and mixtures thereof.

13. The process according to claim 11, wherein said dialkylamine is di-n-propylamine.

14. The process according to claim 11, wherein said dialkylamine is di-n-butylamine.

15. The process according to claim 11, wherein the bromination takes place in the presence of an alcohol.

16. The process according to claim 11, wherein said reaction occurs at a temperature in the range between about −5° C. to 55° C.

17. The process according to claim 11, wherein said reaction is carried out in a single reactor.

18. The process according to claim 7, wherein said phenothiazine and said amine are mixed together in a single reactor, and thereafter said halogen is added.

* * * * *